(12) United States Patent
Heeger et al.

(10) Patent No.: US 11,454,625 B1
(45) Date of Patent: *Sep. 27, 2022

(54) RAPID TESTING MECHANISM AND METHOD FOR RESPIRATORY VIRAL PATHOGENS

(71) Applicants: Brandon Heeger, Avon, IN (US); Ajay Lajmi, Pensacola, FL (US)

(72) Inventors: Brandon Heeger, Avon, IN (US); Ajay Lajmi, Pensacola, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/500,126

(22) Filed: Oct. 13, 2021

Related U.S. Application Data

(63) Continuation of application No. 17/224,076, filed on Apr. 6, 2021.

(60) Provisional application No. 63/016,335, filed on Apr. 28, 2020.

(51) Int. Cl.
| | |
|---|---|
| *G01N 33/497* | (2006.01) |
| *C08B 37/00* | (2006.01) |
| *G01N 33/569* | (2006.01) |
| *A61B 5/08* | (2006.01) |

(52) U.S. Cl.
CPC ........... *G01N 33/497* (2013.01); *A61B 5/082* (2013.01); *C08B 37/0075* (2013.01); *G01N 33/56983* (2013.01)

(58) Field of Classification Search
CPC ..... A61B 5/082; A61B 5/097; C08B 37/0075; G01N 33/56983
See application file for complete search history.

(56) References Cited

U.S. PATENT DOCUMENTS

2021/0321903 A1* 10/2021 Daniels ................. A61B 5/082

* cited by examiner

*Primary Examiner* — Pya Agahi
(74) *Attorney, Agent, or Firm* — C. John Brannon; Brannon Sowers & Cracraft PC

(57) ABSTRACT

A rapid testing mechanism for respiratory viral pathogens includes a filter material positioned to capture exhaled breath particles from a respiratory tract. A portion of the filter material is impregnated with a pathogen binding adsorptive reagent. When the exhaled breath particles pass through the filter material the following occurs: when the binding adsorptive reagent reacts, a positive test for respiratory viral pathogens is indicated by the filter material; and when pathogen binding adsorptive reagent does not react, a negative test for respiratory viral pathogens is indicated by the filter material.

15 Claims, 1 Drawing Sheet

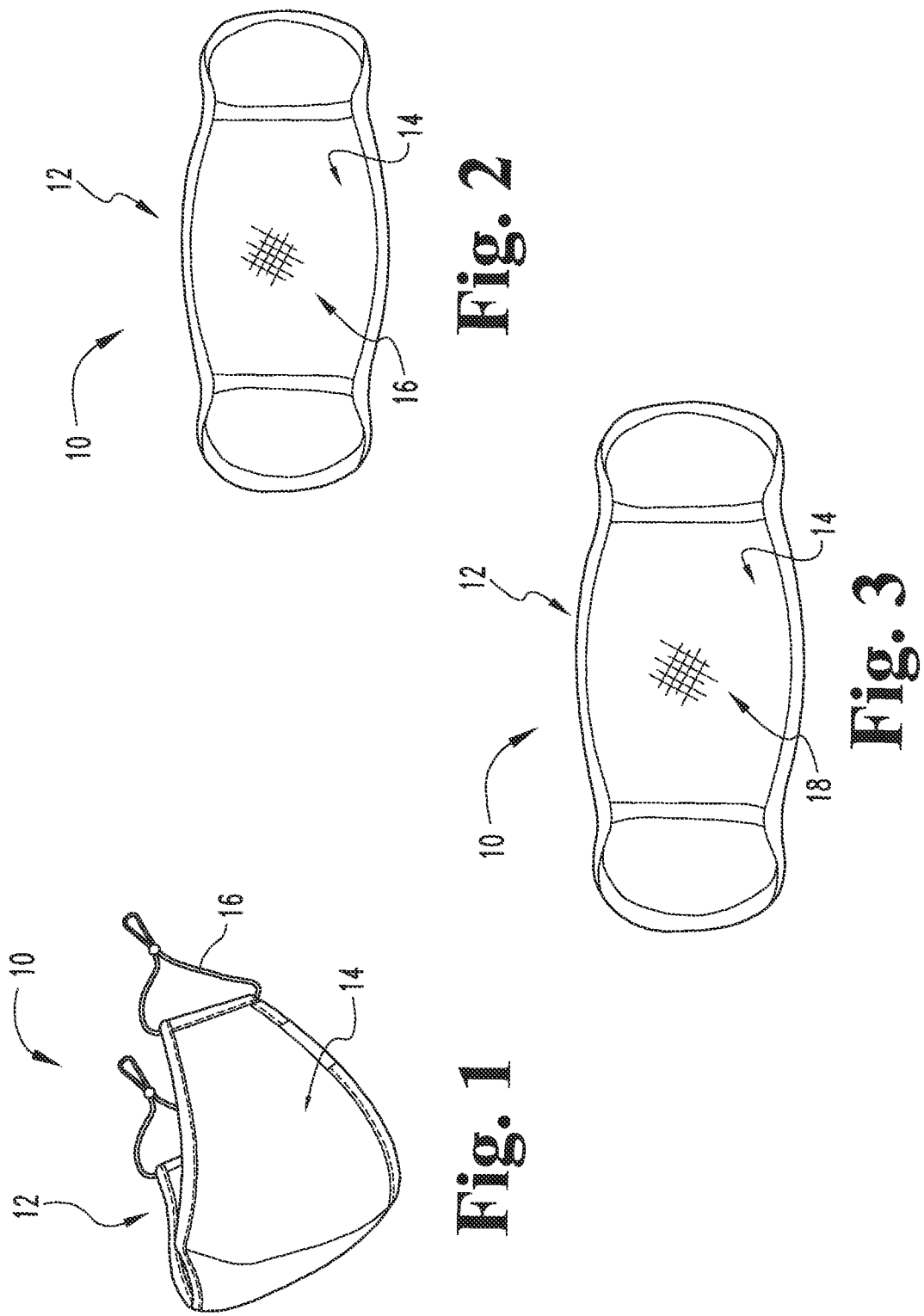

RAPID TESTING MECHANISM AND METHOD FOR RESPIRATORY VIRAL PATHOGENS

CROSS-REFERENCE TO RELATED APPLICATIONS

This patent application is a continuation of U.S. patent application Ser. No. 17/224,076, filed on Apr. 6, 2021, which claimed the benefit under 35 U.S.C § 119(e) of then U.S. Provisional Patent Application Ser. No. 63/016,335, filed on Apr. 27, 2020, which are incorporated herein by reference in their entirety.

TECHNICAL FIELD

The present disclosure relates to the field of respiratory viral pathogen testing. More specifically, the present invention is directed to a rapid mechanism and method for respiratory viral pathogen testing.

BACKGROUND

Conventionally, viral testing is aimed to identify a specific virus. In most situations, identifying a specific virus allows for the collection of epidemiological data and the opportunity for targeted treatment. For example, a patient diagnosed with a viral infection due to influenza might be provided with a prescription of antiviral medication.

However, for the vast majority of respiratory viruses, identifying the specific virus provides little benefit, as the treatment, including supportive care, does not change. As such, testing causes unnecessary cost and burden on the healthcare system. Similarly, there is currently little to no utility in screening asymptomatic individuals, outside of a pandemic or other unique situation.

In the setting of a pandemic, such as when a novel virus is involved, there is typically a lapse in development, production, and distribution of novel viral detection agents. This time delay allows for viral spread without epidemiologic data. Further complicating the scenario are asymptomatic carriers, such as with the recent COVID-19 pandemic. Identifying asymptomatic carriers has proven to be a unique challenge, and the lack of identification of asymptomatic carriers undoubtedly contributes to disease spread. For example, a person who is admitted to the hospital, without clinical evidence of a respiratory virus, might in fact be carrying, and spreading, the COVID-19 virus.

Due to testing limitations, including availability, cost, resource utilization, and time delay until test result, these individuals entering the hospital are typically not screened. They might be admitted to the hospital and spread the disease, unbeknownst to them and the numerous hospital employees they encounter. A similar scenario occurs even when cursory screening is deployed. For example, in the beginning of the COVID-19 pandemic people were being screened for the virus by answering a screening questionnaire and testing for the presence of a fever. This screening is low yield, especially when considering asymptomatic carriers. Innumerable scenarios such as the above could be described.

The present technology is directed to and addresses the issues identified above.

SUMMARY

According to one aspect of the present disclosure, a rapid testing mechanism for respiratory viral pathogens includes a filter material positioned to capture exhaled breath particles from a respiratory tract. A portion of the filter material is impregnated with a pathogen binding adsorptive reagent. When the exhaled breath particles pass through the filter material, the following occur: when the binding adsorptive reagent reacts, a positive test for respiratory viral pathogens is indicated by the filter material; and when the pathogen binding adsorptive reagent does not react, a negative test for respiratory viral pathogens is indicated by the filter material.

According to another aspect, a method of testing for respiratory viral pathogens includes steps of impregnating at least a portion of a filter material with a pathogen binding adsorptive reagent and capturing exhaled breath particles from a respiratory tract with the filter material. A positive test for respiratory viral pathogens is indicated by the filter material when the pathogen binding adsorptive reagent reacts. A negative test for respiratory viral pathogens is indicated by the filter material when the pathogen binding adsorption reagent does not react.

The details of one or more embodiments of the subject matter described in this specification are set forth in the accompanying drawings and the description below. Other features, aspects, and advantages of the subject matter will become apparent from the description, the drawings, and the claims.

BRIEF DESCRIPTION OF THE DRAWINGS

FIG. 1 is a simplified view of a face mask, according to an exemplary embodiment of the present disclosure;

FIG. 2 is simplified view of another face mask, indicating a positive test for respiratory viral pathogens; and FIG. 3 is a simplified view of another face mask, indicating a negative test for respiratory viral pathogens.

Like reference numbers and designations in the various drawings indicate like element.

DETAILED DESCRIPTION

Before the present methods, implementations, and systems are disclosed and described, it is to be understood that this invention is not limited to specific methods, specific components, implementation, or to particular compositions, and as such may, of course, vary. It is also to be understood that the terminology used herein is for the purpose of describing particular implementations only and is not intended to be limiting.

As used in the specification and the claims, the singular forms "a," "an" and "the" include plural references unless the context clearly dictates otherwise. Ranges may be expressed in ways including from "about" one particular value, and/or to "about" another particular value. When such a range is expressed, another implementation may include from the one particular value and/or to the other particular value. Similarly, when values are expressed as approximations, for example by use of the antecedent "about," it will be understood that the particular value forms another implementation. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not. Similarly, "typical" or "typically" means that the subsequently described event or circumstance often though may not occur, and that the description includes instances where said event or circumstance occurs and instances where it does not.

The present disclosure relates generally to a rapid testing mechanism for respiratory viral pathogens. As shown in FIG. 1, an exemplary mechanism for facilitating the rapid testing may include a substrate housing structure 10, such as a face mask 12. The face mask 12, according to one embodiment, may comprise a material, such as filter material 14, straps/ear loops 16 to secure proper positioning of the face mask 12 on the face of a wearer, and a nose wire, which may also be used for positioning.

Typically, the filter material 14 is made up of multiple layers of material. For example, the filter material 14 may be a three-ply material including a melt-blown polymer, such as polypropylene, polyethylene, or vinyl, between non-woven fabric. Numerous factors, such as, for example, shape, size, thickness, number of layers, materials used, fit, breathability, filtering capabilities, disposability, etc. may all be considered, and may vary depending on the application. Additional layers may provide more filtration; however, different materials provide different filtering. Various alternatives to face masks 12 may also be used in combination with the teachings of the present disclosure.

The face mask 12, or an alternative, may be positioned to capture exhaled breath particles from a respiratory tract of a mammal. For example, the face mask 12 may be positioned to cover the mouth and nose of the mammal and capture breath particles in one or more layers of the filter material 14. According to an exemplary embodiment, a layer closest to the source of the exhaled breath particles may be a filter. Some household items may work as a filter layer in a homemade mask, including, for example, paper products that you can breathe through, such as coffee filters, paper towels, and toilet paper. As described above, various structures, materials and configurations may be incorporated into the present disclosure.

Knowing the average size of a virus is about 20-400 nanometers (0.02-0.4 microns), the filter material 14 may capture particles greater than about 400 nanometers (0.4 micrometers). This may allow viruses or viral particles to pass through the filter material 14. For example, the novel coronavirus is approximately 0.12 micrometers, so the novel coronavirus would pass freely through the filter material 14, but a bacteria that is 0.2 micrometers would be stopped by the filter material 14. However, most viral particles do not travel independently, but are carried by larger media, such as water droplets, that would be stopped by the filter. This filtering method is provided for exemplary purposes only and other filtering methods may be used. Further, one or more of the filtering methods may be implemented to narrow the viral pathogens that are detected.

At least a portion of the filter material 14 and/or another layer and/or another material is impregnated with a pathogen binding adsorptive reagent. According to exemplary embodiments, the pathogen binding adsorptive reagent may be heparin sepharose or sulfated cellulose, which may have a pore size of >0.4 micron. Although the amounts of the reagent may vary, according to an exemplary embodiment, the filter material 14 may be impregnated with 0.3 mL of the pathogen binding adsorptive reagent.

According to some embodiments, heparin-based porous absorptive beads are combined with glycerine to slow the drying and extend viability. Further, the housing structure for the filter may be packaged in a porous polymeric membrane.

When the face mask 12 is analyzed, if the binding adsorptive reagent reacts, a positive test for the respiratory viral pathogens is indicated by the filter material 14, as shown at 16 in FIG. 2. According to the exemplary embodiment, the indicator may be a particular color for a positive test. However, various different indicators may be used.

If the pathogen binding adsorptive reagent does not react, a negative test for respiratory viral pathogens is indicated by the filter material 14, as shown at 18 in FIG. 3. For example, a color different from the color indicating a positive test, may be used to indicate a negative test.

In addition to the filtering, the disclosure utilizes affinity chromatography to signify the presence of a virus or viral particles, regardless of the speciation. Non-viral material that is less than 400 nanometers may pass through the filter but will not react with the reagent. This is a low cost, highly sensitive, and qualitative test that is not labor intensive, not prone to operator variation (i.e., correct placement of nasopharyngeal swabs), or reliant on expensive, advanced technology. This technology could be available for home or commercial testing or healthcare point of care testing. The design would allow it to be deployed in resource poor countries. This test may have other novel implications, such as screening mammals (humans or animals) for the presence of contagious diseases before boarding aircraft, within closed spaces, or other places where there might be an increased risk of disease transmission, irrespective of a pandemic state. As stated above, the filter is not restricted to use with a face mask. For example, the filter may be positioned within an aircraft, classroom, office etc. to detect a presence of the virus.

The present disclosure provides a quick and accurate means for detecting viruses that are aerosolized or expelled from the respiratory tract during breathing, coughing, or sneezing. The disclosure exploits commonalities in the composition of viruses expelled from the respiratory tract of a mammal.

Benefits of the disclosure also include the provision of a rapid qualitative assessment for respiratory viral pathogens, which disregards speciation in the immediacy. Using this highly sensitive, rapid, and qualitative assessment for respiratory viral pathogens, regardless of speciation, could assist in implementing proper triage, proper precautions could be taken, and more specific testing could be imposed, if indicated.

Particular embodiments of the subject matter have been described. Other embodiments are within the scope of the following claims.

We claim:

1. A rapid testing mechanism for respiratory viral pathogens, including:

a filter material positioned to capture exhaled breath particles from a respiratory tract;

wherein at least a portion of the filter material is impregnated with a heparin sepharose pathogen binding adsorptive reagent;

wherein, when the exhaled breath particles pass through the filter material, the following occur:

when the binding adsorptive reagent reacts, a positive test for respiratory viral pathogens is indicated by the filter material; and when the pathogen binding adsorptive reagent does not react, a negative test for respiratory viral pathogens is indicated by the filter material.

2. The rapid testing mechanism of claim 1, wherein the filter material is impregnated with greater than 0.2 mL of the pathogen binding adsorptive reagent.

3. The rapid testing mechanism of claim 1, wherein the filter material includes multiple layers.

4. The rapid testing mechanism of claim 1, including a porous sealed packet containing the pathogen binding adsorptive reagent.

5. The testing mechanism of claim 4, wherein the porous sealed packet is positioned between two layers of multiple layers of the filter material.

6. The testing mechanism of claim 1, wherein the respiratory viral pathogens include ribonucleic acid viruses.

7. The testing medium of claim 1, wherein the filter material is a face mask covering a nose and mouth of a wearer.

8. The testing medium of claim 1, wherein a heparin-based porous absorptive beads are combined with glycerine.

9. The testing medium of claim 1, wherein a housing structure for the filter may be packaged in porous polymeric membrane polyethylene.

10. A method of testing for respiratory viral pathogens, including steps of:
 impregnating at least a portion of a filter material with a heparin sepharose pathogen binding adsorptive reagent;
 capturing exhaled breath particles from a respiratory tract with the filter material;
 indicating, by the filter material, a positive test for respiratory viral pathogens when the pathogen binding adsorptive reagent reacts; and
 indicating, by the filter material, a negative test for respiratory viral pathogens when the pathogen binding adsorptive reagent does not react.

11. The method of claim 10, further including:
 impregnating the filter material with greater than 0.2 mL of the pathogen binding adsorptive reagent.

12. The method of claim 10, further including:
 providing the filter material with multiple layers.

13. The method of claim 10, further including:
 containing the pathogen binding adsorptive reagent within a porous sealed packet.

14. The method of claim 10, wherein the respiratory viral pathogens include ribonucleic acid viruses.

15. The method of claim 10, further including:
 providing a face mask including the impregnated filter material covering a nose and mouth of a wearer.

\* \* \* \* \*